US011021313B2

(12) United States Patent
Garcia Earley et al.

(10) Patent No.: US 11,021,313 B2
(45) Date of Patent: Jun. 1, 2021

(54) ENZYME FORMULATIONS, DEVICES AND METHODS OF USE

(71) Applicant: BuzzBite, LLC, Chicago, IL (US)

(72) Inventors: Alejandra Garcia Earley, Chicago, IL (US); Erika Milczek, New York, NY (US)

(73) Assignee: BUZZBITE, LLC, Chicago, IL (US)

( * ) Notice: Subject to any disclaimer, the term of this patent is extended or adjusted under 35 U.S.C. 154(b) by 76 days.

(21) Appl. No.: 16/103,190

(22) Filed: Aug. 14, 2018

(65) Prior Publication Data

US 2019/0047769 A1    Feb. 14, 2019

Related U.S. Application Data

(60) Provisional application No. 62/545,274, filed on Aug. 14, 2017.

(51) Int. Cl.
| | |
|---|---|
| *B65D 81/32* | (2006.01) |
| *A61P 17/08* | (2006.01) |
| *A61P 17/04* | (2006.01) |
| *A61P 17/06* | (2006.01) |

(52) U.S. Cl.
CPC ...... *B65D 81/32* (2013.01); *C12Y 304/22032* (2013.01); *C12Y 304/22033* (2013.01); *A61P 17/04* (2018.01); *A61P 17/06* (2018.01); *A61P 17/08* (2018.01)

(58) Field of Classification Search
CPC ............ B65D 81/32; C12Y 304/22032; C12Y 304/22033; A61P 17/08; A61P 17/04; A61P 17/06
USPC ................................................... 424/94.065
See application file for complete search history.

(56) References Cited

U.S. PATENT DOCUMENTS

| | | | |
|---|---|---|---|
| 4,959,179 A | | 9/1990 | Aronson |
| 5,543,149 A | * | 8/1996 | Rubin ................... A61K 38/465 |
| | | | 424/405 |
| 6,303,119 B1 | | 10/2001 | Weisgerber |
| 2005/0106224 A1 | * | 5/2005 | Qvist ....................... A61J 1/067 |
| | | | 424/445 |
| 2007/0110739 A1 | | 5/2007 | Logsdon |
| 2010/0104547 A1 | | 4/2010 | Logsdon |
| 2011/0189160 A1 | * | 8/2011 | Bartels .................... A61K 45/06 |
| | | | 424/94.64 |
| 2012/0104047 A1 | * | 5/2012 | Lim ........................ A61K 31/46 |
| | | | 424/43 |
| 2015/0079688 A1 | * | 3/2015 | Kahaian .................. B01L 3/505 |
| | | | 436/79 |
| 2015/0118167 A1 | * | 4/2015 | Boyd ...................... A61Q 11/00 |
| | | | 424/50 |
| 2015/0238576 A1 | | 8/2015 | Richon |
| 2016/0008777 A1 | * | 1/2016 | Patel ..................... B01F 13/0052 |
| | | | 424/94.67 |
| 2016/0361393 A1 | * | 12/2016 | Huggins ................ A61K 36/28 |

FOREIGN PATENT DOCUMENTS

EP    0498532    8/1992

OTHER PUBLICATIONS

Suh, H.J., Lee, H., Cho, H.Y. & Yang, H.C. Purification and characterization of bromelain isolated from pineapple. 1992, J. Korean Agric. Chem. Soc., 35(4), 300-307. (Year: 1992).*

* cited by examiner

*Primary Examiner* — Satyendra K Singh
(74) *Attorney, Agent, or Firm* — Leydig, Voit & Mayer, Ltd.

(57) ABSTRACT

Topical formulations of proteases, devices including the formulations are disclosed. Described herein are packages for storing and dispensing multi-part topical enzyme formulations and neutralizing agent, wherein the contents of the parts are mixed, and the enzyme is taken into solution containing a neutralizing agent (skin protectant) for treatment of skin abrasions and disorders. Particular multi-part topical formulation disclosed here relates to immediate (neutralizing agent) and extended relief (enzymes) from itching and inflammation associated with insect stings, insect bites, contact dermatitis such as poison ivy and poison oak, and eczema. The formulations and packaging using this principle and methods of use thereof are also provided. Additionally this invention contains active ingredients for wound cleaning and debridement.

17 Claims, 1 Drawing Sheet

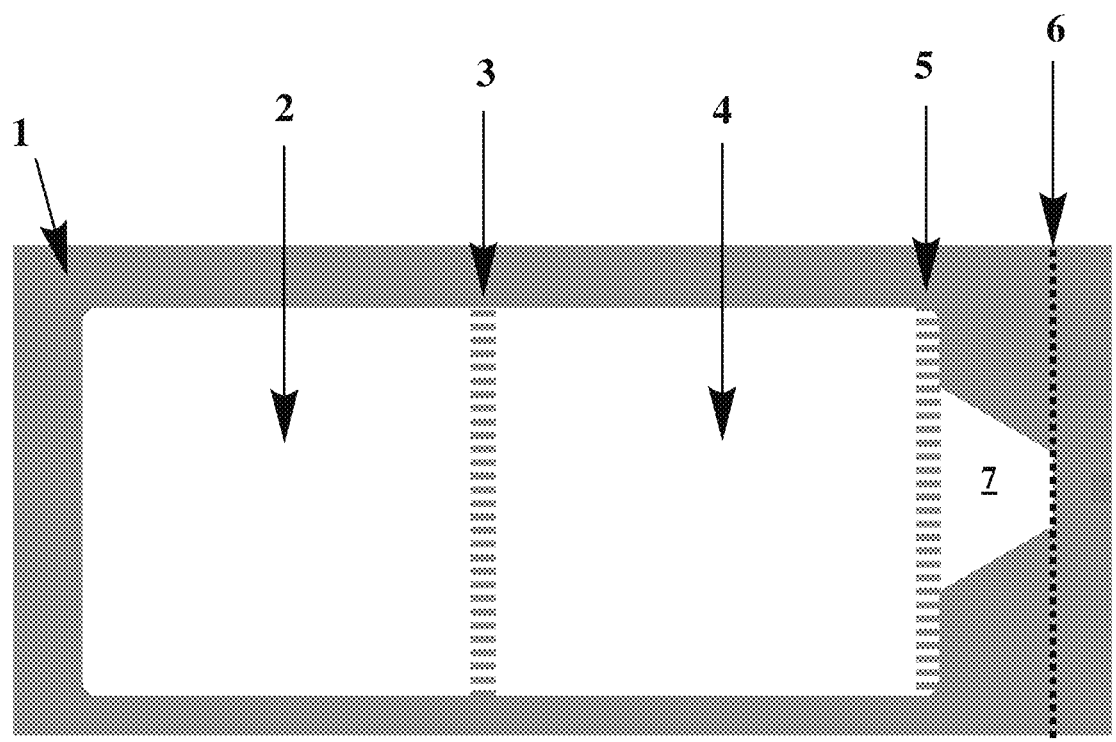

ENZYME FORMULATIONS, DEVICES AND METHODS OF USE

CROSS-REFERENCE TO RELATED APPLICATIONS

This application claims priority to U.S. Ser. No. 62/545,274, filed on Aug. 14, 2017, which is incorporated herein in its entirety.

FIELD OF THE INVENTION

The invention is generally directed to topical formulations including enzymes and methods of use.

BACKGROUND OF THE INVENTION

For years companies have tried to use enzymes in consumer products, particularly personal care products. However there are few commercial examples of enzyme formulations in the market place. These products range from tooth and skin whitening formulations, exfoliants (U.S. Pat. No. 6,303,119 B) anti-itch or venom neutralizing [US Publication Nos. 2007/0110739, 2015/0238576, and 2010/0104547], and wound debridement formulations [European patent 92300228.1]. Unfortunately, these products have not been successful brought to market, due to poor enzyme stability in solution. A notable successful example is that of household cleaning products like laundry detergent where cellulases, lipases, and proteases are co-formulated in liquid laundry detergent. These are highly stable enzymes that are manufactured on the metric ton scale by enzyme manufacturers after years of enzyme engineering to maximize the enzymes' stability in solution and at room temperature. For this reason subtilisin is the most common protease found in consumer products to date.

Developing shelf stable liquid formulation of protease enzymes is difficult because of their ability to proteolyze proteins, including autoproteolysis. Shelf stable liquid preparation of proteases containing products can be achieved by adding stabilizers, or inhibitors, to the protease prior to mixing with other enzymes [U.S. Pat. No. 4,959,179]. Primarily the inhibitors are non-covalent, reversible inhibitors that require dilution of the enzyme-inhibitor complex to afford active enzyme. These are imperative for products contain a protease in solution to inhibit protease activity, which prevents auto-degradation as well as degradation of other proteins and enzymes in the mixture to smaller peptides or simple amino acids. Therefore an inhibitor of the protease allows for shelf stable formulations overtime. Unfortunately this method requires dilution of the enzyme-inhibitor complex to regain activity, which is easily achieved in the detergent industry by adding detergent to the washing machine with additional water added as well. However, this is not a viable strategy for many topical formulations where dilution of the topical is impractical. Moreover, inhibitors and stabilizers change the sensory qualities of the topical, may be incompatible with other ingredients in the topical formulation and may not be available in USP or NF quality preparation for topical pharmaceutical use.

Many active proteins, including enzymes, are potential antigens, and may cause allergic reactions in humans. The human immune system can produce specific antibodies upon exposure to active proteins. This process of producing specific antibodies is referred to as "immunization" when a clinically beneficial response is obtained. When the response leads to hypersensitivity, however, it is referred to as "sensitization." Allergenic sensitization to active proteins has been observed in environments where humans are regularly exposed to the protein. Such environments include manufacturing facilities, where workers can be exposed to uncontrolled dust or aerosol containing an active protein, or the marketplace, where consumers' repeated use of products containing active proteins has, on occasion, caused an allergic reaction. Allergic responses to active proteins can be minimized by limiting the selection of those proteins used in products to those of human origin. While this approach minimizes allergenicity problems, it is not a complete solution since it is often not possible to find such an active protein which also has the activity properties desired. Another way of diminishing allergic response has been to reduce the size of the protein molecules. However, size reduction may also cause a significant reduction in enzyme activity. A third approach for decreasing allergenicity is through epitope mapping and alteration of the protein amino acid sequence to deliver a protein with reduced allergenicity. Still another approach includes attaching unreactive polymers such as polyethylene glycol to the protein. Immobilizing or covalently functionalizing the enzyme does reduce exposure to airborne protein particles but does not reduce consumer exposure to extended tissue contact with the released enzyme which is deposited on the skin and can also result in allergenic response. It would be highly desirable to develop a composition which would provide improved levels of protein activity while maintaining low allergenic responses from exposure to the active proteins Therefore there is still a need for packaging options for use of enzymes, for example, hydrolases, in topical formulations that would lend to a long shelf life or increased stability over time without the addition of unnecessary stabilizers while minimizing the allergenicity problems associated with repeated exposure to active proteins.

It is an object of the present invention to provide formulations and devices which deliver improved protein activity while maintaining reduced stimulation of and resulting activation of the immune system by maintaining very low doses of the protein.

It is also an object of the present invention to provide a device for maintaining protein stability over time, which provides highly active protein upon application.

It is also an object of the present invention to provide a method for topical delivery of active proteins, while minimizing allergenicity of the protein.

SUMMARY OF THE INVENTION

Topical formulations of enzymes, devices including the formulations are provided which include reduced amounts of protease while maintaining efficacy. A preferred enzyme is a protease, more preferably, bromelain. The formulations are provided in a multi-chamber system which includes an outlet, and at least two chambers separated by a frangible or tearable seal. One chamber of the multi-chamber system contains a composition, for example, liquid solution, a dermatological carrier, for example, gel or ointment for enhancing enzyme activity ("diluent chamber) and another contains a liquid, powder or mixture of powders of enzyme ("enzyme chamber"). Upon rolling or squeezing either chamber, the barrier between the chambers breaks and the components of the chambers can be mixed to provide a protease in a highly reactive environment for enhancing proteolytic activity. In a preferred embodiment, the components of the diluent and protease chambers form a solution, emulsion, suspension or extrudable gel when mixed. The mixture can be dispensed through an outlet in the second chamber to a site in need thereof, providing effective treatment in a shorter period and with lower enzyme levels.

The disclosed formulations are applied to a site in need of an anti-itch, anti-inflammatory, wound cleanser, skin conditioning formulation or for removal of dead skin.

BRIEF DESCRIPTION OF THE DRAWINGS

FIG. 1 show a view of an embodiment device with frangible seals. The device includes a heat sealed outer perimeter (1); including a heat sealed outer perimeter (1); a diluent chamber (2); a first breakable, tearable, or frangible seal (3); an enzyme (4); an optional second breakable, tearable, frangible seal (5); a perforated/scored tearable line (6) and a spout/nozzle (7) to dispense the product.

DETAILED DESCRIPTION OF THE INVENTION

I. Definitions

"Cosmetically acceptable" refers to those compounds, materials, compositions, or dosage forms which are, within the scope of sound medical judgment, suitable for use in contact with the tissues of human beings without excessive toxicity, irritation, allergic response, or other problems or complications commensurate with a reasonable benefit/risk ratio.

"Gel" as used herein is a colloid in which the dispersed phase has combined with the continuous phase to produce a semisolid material, such as jelly.

The use of the terms "a," "an," "the," and similar referents in the context of describing the presently claimed invention (especially in the context of the claims) are to be construed to cover both the singular and the plural, unless otherwise indicated herein or clearly contradicted by context.

Recitation of ranges of values herein are merely intended to serve as a shorthand method of referring individually to each separate value falling within the range, unless otherwise indicated herein, and each separate value is incorporated into the specification as if it were individually recited herein.

Use of the term "about" is intended to describe values either above or below the stated value in a range of approx. +/−10%; in other embodiments the values may range in value either above or below the stated value in a range of approx. +/−5%; in other embodiments the values may range in value either above or below the stated value in a range of approx. +/−2%; in other embodiments the values may range in value either above or below the stated value in a range of approx. +/−1%. The preceding ranges are intended to be made clear by context, and no further limitation is implied. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

II. Compositions and Devices

The compositions and devices disclosed herein provide a tearable seal device that allows separation of enzyme from its activating solution until usage. The devices can be configured to allow for storage of the enzyme formulation once mixed, for example, by including a screw cap, ziplock, or an adhesive closure. The device and compositions disclosed herein avoids over dosing of enzymes in personal care preparation because low enzyme concentrations are included in the devices, maintained out of contact with it activating solution, and combined with the activating solution at the time of usage to provide therapeutically effective enzyme activity. By using the minimum necessary amount of enzyme and stabilizing it over time, high amounts of enzyme is not needed to ensure high activity at the point of sale/use. This ultimately reduces the risk of allergic reaction of the active protein by the user. This is important because having low concentrations of enzymes reduces the risk of contact dermatitis, which is frequently an issue with high dosages of enzymes.

A. Enzymes and Diluents (i) Enzymes and Enzyme Chamber

Examples of useful enzyme(s) include proteases, (bromelain, papain, subtilisin, and ficin), lipases, peroxidase and cellulase enzymes. The enzymes can be obtained from a commercially available source or prepared from natural sources. For example, the bromelain source may be a crude bromelain extract isolated from pineapple and sold as a mixture of enzymes (with protease, cellulase, and peroxidase activity) in maltodextrin which can be included in the enzyme chamber.

In a particularly preferred embodiment however, the enzyme chamber does not include an emulsion, and the enzymes are preferably included in the enzyme chamber in powder form. In a more preferred embodiment, the enzyme concentration does not exceed 1 wt % active enzyme when mixed with the diluent chamber. The enzyme is retained in powder form until the seal between enzyme and diluent chambers is broken and the contents of the two chambers, mixed.

In some preferred embodiments, the concentration of the enzyme included in the enzyme chamber should provide a bromelain concentration ranging from 0.007 to 1 wt %, when combined with the components of the diluent chamber, and in even more preferred embodiments, between 0.01 wt % and 0.22 wt %, most preferably, between 0.148 wt % to 0.222 wt %.

(ii) Diluents and Diluent Chamber

The diluent contains an anti-itch drug, for example, sodium bicarbonate, or composition for enhancing protease activity in the form of a liquid solution, gel or ointment. The diluent chamber preferably contains a liquid solution or gel whose pH is controlled using a buffer such as sodium bicarbonate, ammonia, borate salts, or other pH altering substance. The anti-itch drug or buffer is included in the diluent chamber in an amount ranging from 0.1 to 20 wt %, preferably between 1 and 10 wt % and more preferably, between 1 and 5 wt %, for example, 1, 2, 3, 4, or 5 wt % of the contents of the diluent chamber.

The contents of the diluent chamber are preferably at a pH range between pH 7.1-9.5, preferably between 7-9, more preferably, between 7.8 and 9.0, and even more preferably, between 8.0 and 9.0. A most preferred pH is 8.5.

This chamber can include cosmeceutically or dermatologically acceptable topical carrier/excipients. Suitable cosmetically acceptable excipients include, but are not limited to, water, chelating agents, emulsifiers, thickeners, feel modifiers, preservatives, humectants, emollients, hydratants, antioxidants, pH adjusting agents (e.g., citric acid, sodium hydroxide), soft focus agents, moisturizing agents, sunscreen agents, vitamins, dyes, pigments proteins, amino acids, fragrances, perfumes, oils, lubricants, butters, penetrants, viscosity modifiers, polymers, resins, film formers, surfactants, detergents, opacifying agents, volatiles, propellants, liquid vehicles, carriers, salts, neutralizing agents, buffers, absorbents, viscosity modifying agents and combinations thereof. The composition can contain one or more pigments.

This chamber may also contain components for stabilizing the enzyme in solution such as polyols like glycerol, sorbate, corn sugar, or other enzyme stabilizers.

Additionally, the viscose liquid may contain an activity enhancing agent such as a benzoate that can also function as an anti-microbial (benzoate enhances the enzyme activity while acting as an anti-microbial).

"Preservatives" can be used to prevent the growth of fungi and microorganisms. Suitable antifungal and antimicrobial agents include, but are not limited to, benzoic acid, butylparaben, ethyl paraben, methyl paraben, propylparaben, benzoates, for example, sodium benzoate, sodium propionate, benzalkonium chloride, benzethonium chloride, benzyl alcohol, cetylpyridinium chloride, chlorobutanol, phenol, phenylethyl alcohol, and thimerosal. A preferred preservative is sodium benzoate. The preservative can be included in an amount ranging from 0.01 wt % to 10 wt %, preferably, between 0.1 and 5 wt %, more preferably, between 0.1 and 2 wt %.

A most preferred diluent contains water, glycerol (20 wt %), sodium bicarbonate (5.25 wt %), xanthan gum (or other orally safe viscosity enhancing agent such as polysaccharides at 0.8 wt %), sodium benzoate (1 wt %) at pH 8.5 as a colorless gel.

The contents of the diluent chamber are preferably at a pH range between pH 7.1-9.5, more preferably, between 7.8 and 8.0. Accordingly, the diluent and/or enzyme chambers preferably do not include pH lowering agents or agents which react to form pH lowering species. None of the chambers preferably include a peroxide source, peracids or oxidants such as dioxirane The diluent chamber includes between 1 and 15 ml, more preferably, between 5 and 10 ml, and even more preferably, about 5 ml.

B. Topical Formulations

Suitable dosage forms for topical administration include creams, ointments, salves, sprays, gels, lotions and emulsions. Accordingly, the component of the diluent chamber can be formulated such that its mixture with the components of the enzyme chamber results in a cream, ointment, salve, spray, gel, lotion or emulsions.

Upon mixing of the contents of the chambers, the protein having protease, cellulase, and peroxidase activity (such as stem bromelain) is brought into an environment that promotes activity. This reactive enzyme solution is then applied to the skin, so that effective skin conditioning action can be achieved in a shorter period and with lower enzyme levels.

In some embodiments, a preferred topical formulation includes an anti-itch drug such as sodium bicarbonate, bromelain and/or colloidal oatmeal. In these embodiments the colloidal oatmeal is provided in the enzyme chamber, with the contents of the diluent chamber being as described herein.

A preferred topical formulation includes a bromelain contention between 0.01 wt % and 1 wt % bromelain in dermatological carrier to deliver the desired therapeutic response, most preferably, between 0.148 wt % to 0.222 wt %.

(i) Gels

A gel typically contains dispersions of small or large molecules in a liquid vehicle that is rendered semisolid by the action of a thickening agent or polymeric material dissolved or suspended in the liquid vehicle. The liquid may include a lipophilic component, an aqueous component or both. Some emulsions may be gels or otherwise include a gel component. Some gels, however, are not emulsions because they do not contain a homogenized blend of immiscible components. Suitable gelling agents include, but are not limited to, modified celluloses, such as hydroxypropyl cellulose and hydroxyethyl cellulose; Carbopol homopolymers and copolymers; and combinations thereof. The gelling agents can make up 0.005 to 10 wt % of the diluent chamber components, for example, between 0.05 wt % to 5 wt %, more preferably, between 0.05% to 2 wt % and even more preferably, between 0.1 and 0.8 wt %. Suitable solvents in the liquid vehicle include, but are not limited to, diglycol monoethyl ether; alklene glycols, such as propylene glycol; dimethyl isosorbide; alcohols, such as isopropyl alcohol and ethanol. The solvents are typically selected for their ability to dissolve the drug. Other additives, which improve the skin feel and/or emolliency of the formulation, may also be incorporated. Examples of such additives include, but are not limited, isopropyl myristate, ethyl acetate, C12-C15 alkyl benzoates, mineral oil, squalane, cyclomethicone, capric/caprylic triglycerides, and combinations thereof.

(ii) Emulsions

An emulsion is a preparation of one liquid distributed in small globules throughout the body of a second liquid. In particular forms, the non-miscible components of the emulsion include a lipophilic component and an aqueous component. The dispersed liquid is the discontinuous phase, and the dispersion medium is the continuous phase. When oil is the dispersed liquid and an aqueous solution is the continuous phase, it is known as an oil-in-water emulsion, whereas when water or aqueous solution is the dispersed phase and oil or oleaginous substance is the continuous phase, it is known as a water-in-oil emulsion. Either or both of the oil phase and the aqueous phase may contain one or more surfactants, emulsifiers, emulsion stabilizers, buffers, and other excipients. Preferred excipients include surfactants, especially non-ionic surfactants; emulsifying agents, especially emulsifying waxes; and liquid non-volatile non-aqueous materials, particularly glycols such as propylene glycol. The oil phase may contain other oily pharmaceutically approved excipients. For example, materials such as hydroxylated castor oil or sesame oil may be used in the oil phase as surfactants or emulsifiers.

The oil phase may consist at least in part of a propellant, such as an HFA propellant. Either or both of the oil phase and the aqueous phase may contain one or more surfactants, emulsifiers, emulsion stabilizers, buffers, and other excipients. Preferred excipients include surfactants, especially non-ionic surfactants; emulsifying agents, especially emulsifying waxes; and liquid non-volatile non-aqueous materials, particularly glycols such as propylene glycol. The oil phase may contain other oily pharmaceutically approved excipients. For example, materials such as hydroxylated castor oil or sesame oil may be used in the oil phase as surfactants or emulsifiers.

(iii) Lotions

A lotion can contain finely powdered substances that are in soluble in the dispersion medium through the use of suspending agents and dispersing agents. Alternatively, lotions can have as the dispersed phase liquid substances that are immiscible with the vehicle and are usually dispersed by means of emulsifying agents or other suitable stabilizers. In some forms, the lotion is in the form of an emulsion having a viscosity of between 100 and 1000 centistokes. The fluidity of lotions permits rapid and uniform application over a wide surface area. Lotions are typically intended to dry on the skin leaving a thin coat of their medicinal components on the skin's surface.

(iv) Creams

Creams may contain emulsifying agents and/or other stabilizing agents. In some forms, the formulation is in the form of a cream having a viscosity of greater than 1000 centistokes, typically in the range of 20,000-50,000 centistokes. Creams are often time preferred over ointments, as they are generally easier to spread and easier to remove.

The difference between a cream and a lotion is the viscosity, which is dependent on the amount/use of various oils and the percentage of water used to prepare the formulations. Creams are typically thicker than lotions, may have various uses and often one uses more varied oils/butters, depending upon the desired effect upon the skin. In a cream formulation, the water-base percentage is about 60-75% and the oil-base is about 20-30% of the total, with the other percentages being the emulsifier agent, preservatives and additives for a total of 100%.

C. Oral Formulations

One embodiment provides liquid dosage forms following mixing of the components of enzyme and diluent chambers for oral administration, including pharmaceutically acceptable emulsions, solutions, suspensions, and syrups, which may contain other components including inert diluents; adjuvants such as wetting agents, emulsifying and suspending agents; and sweetening, flavoring, and perfuming agents.

Oral formulations can include standard carriers such as pharmaceutical grades of mannitol, lactose, sodium saccharine, starch, magnesium stearate, cellulose, magnesium carbonate, etc.

A preferred oral formulation includes sodium bicarbonate and bromelain.

D. Devices

Bromelain and subtilisins are examples of proteases useful in the methods disclosed herein. When in the solid form, these enzymes have stability of many years at room temperature with modest loss in activity due to moisture and oxygen exposure. Neutral to slightly alkaline conditions (pH 6.8-9, preferably, 7.4-8.5) are better for proteolytic activity but are detrimental to enzyme stability over time. This is largely due to autoproteolysis.

Accordingly, the devices herein employ a deformable material and frangible seal technology to separate the enzymes from the alkaline diluent until mixing is desired. Frangible seal technology enables the controlled release of testing reagents, eliminating the need for complex fluid handling systems. Frangible sealed reservoirs use differential weld strengths that are designed to fail under specific pressures, allowing for a unit-of-use measure to be precisely delivered to a target well or reaction zone, Therefore, preferably, the device omits additional puncture members required to introduce the contents of the first chamber into the second chamber.

Preferable deformable materials include aluminum and plastic.

An exemplary device is shown in FIG. 1. The device includes a heat sealed outer perimeter (1) (that provides permanent closure that must be torn to open or dispense); a diluent chamber (2) (that holds a neutralizing agent and/or acceptable dermatological carrier); a first breakable, tearable, or frangible seal (3) (that separates the contents of the diluent chamber from the contents of enzyme chamber); an enzyme (4); an optional second breakable, tearable, frangible seal (5); an optional perforated/scored tearable line (6) and a spout/nozzle (7) to dispense the product.

The nozzle in some embodiments include a screw cap for resealing the device after use.

In a preferred embodiment, the heat sealed outer perimeter is the only permanent seal in the device i.e., the device does not include interior permanent seals and/or the frangible seal spans the width of the first and second chambers i.e., the length of the frangible seal separating the enzyme and the diluents chambers is the same as the width or length of the first and second chambers depending on whether the frangible seal is placed lengthwise or widthwise between the first and second chambers. In embodiments where the chambers are square in dimension, the length of the frangible seal if of the same dimension as one side of the chambers.

Materials useful for making the multi-compartment system disclosed herein include high barrier polypropylene films with aluminum packaging for preventing moisture and oxygen exposure.

The films can be opaque or translucent and are preferably flexible. The films can include aluminum in some embodiments.

Flexible films which may be used include those having a permeation of less than 10% product loss/year at 35° C./20% RH. Preferably, this design allows minimal loss of enzyme activity at 40° C. for at least six months.

In some embodiments the film is a laminate film or other multi-layer structure that comprises a high barrier material, such as high barrier PET, metallized PET, aluminum foil, $SiO_2$ or a mixture of these. In some embodiments, the film comprises a laminate itself comprising at least one aluminum layer that gives very good barrier properties to liquids, gas and vapors, for example, a Surlyn®/metallized PET/ LDPE having thicknesses of 50 µm/12 µm/24 µm respectively. Optionally, thermoplastics, such as high-density polyethylene (HDPE) more than 50 µm thick, or polypropylene (PP) more than 100 µm thick, or low-density polyethylene (LDPE) more than 150 µm thick can be used. Even if such materials are not inherently high barrier materials, the thickness used allows good barrier properties.

Films that generally have the characteristic disclosed therein are known in the art, for example, the peelable films available from Glenroy, Inc. (Menomonee Falls, Wis.).

III. Methods of Use

The formulations disclosed herein can be used for the treatment of irritation, itch, pain, and inflammation caused from insect bites, poison ivy, poison oak, or eczema. Other conditions that can be treated with the formulations disclosed herein include burns, contact dermatitis, idiopathic itch, diabetic itch, wound healing, jellyfish stings, psoriasis, rash, rosacea, shingles, seborrhea, chronic itch, or bruising.

In use, the seal of multicompartment system including the enzyme is when the barrier is broken by gently rolling or squeezing either chamber to allow the contents of the chambers to mix. The enzyme is taken into the diluent, and the mixture can be applied to the skin and can react to deliver the desired effect. The contents of the container are dispensed via an opening means. e.g., through a nozzle, which can include a removable cap or plug or which becomes functional when a preferentially scored section of the container is broken off by the consumer, permitting clean and convenient dispensing of product through a shaped nozzle.

Once broken and mixed, the enzyme formulation remains effective and can be reused for a period of up to 2 weeks after mixing.

The compositions are applied in an effective amount to reduce one or more symptoms of the conditions being treated, particularly itching. An effective amount is an amount sufficient to coat the affected area of the skin with a layer of the composition, and will ordinarily be between 0.05 and 1.0 grams per square inch of skin.

In a preferred embodiment the resulting mixture for application to the skin is in the form of a gel. The gel can be applied to the skin so the reaction being catalyzed by the enzyme(s) can be performed in sufficient time, e.g., 5-90 minutes, to afford a skin conditioning affect without having to sit in one position for extended periods of time. The mixture can be applied like a lotion allowing the user to move freely while the product infers its effects quickly and effectively.

The formulations disclosed herein can also be used to remove dead skin/dead cells from a surface in need thereof. Thus, the formulations can be used for oral care, as "oral debriding agent/oral wound cleaner, for temporary use in cleansing minor wounds or gum inflammation resulting from minor dental procedures, dentures, orthodontic appliances, accidental injury, or other irritations of the mouth and gums, for example, canker sores. In some embodiment, the formulation is preferably in the form of a solution. In other embodiments, the formulation is in the form of a gel.

EXAMPLES

Rate of Decomposition Out of Solution (Solid Enzyme)

When solid bromelain or papain is stored in polyethylene film and an aluminum coating at 4° C. activity decreases by less than 10% per year while decreases of 20-30% are observed at room temperature over 2 years.

While in the foregoing specification this invention has been described in relation to certain embodiments thereof, and many details have been put forth for the purpose of illustration, it will be apparent to those skilled in the art that the invention is susceptible to additional embodiments and that certain of the details described herein can be varied considerably without departing from the basic principles of the invention.

All references cited herein are incorporated by reference in their entirety. The present invention may be embodied in other specific forms without departing from the spirit or essential attributes thereof and, accordingly, reference should be made to the appended claims, rather than to the foregoing specification, as indicating the scope of the invention.

We claim:

1. A package comprising:
   a deformable material comprising at least two sealed chambers, the two sealed chambers comprising:
   an enzyme chamber comprising one or more enzymes selected from the group consisting of proteases, lipases, cellulases, and peroxidase, and
   a diluent chamber comprising a diluent at a pH ranging from 7.1 to 9.5,
   wherein the enzyme chamber and the diluent chamber are physically separated by one or more barriers which are frangible or tearable,
   wherein the one or more enzymes is present in an amount of 1 wt % or less, based on total weight of the one or more enzymes and the diluent,
   wherein the diluent comprises water and sodium bicarbonate, and optionally further comprises a viscosity enhancing agent, glycerol, and sodium benzoate, and
   wherein at least one of the chambers is connected to an opening for dispensing the components of the chamber.

2. The package of claim 1, wherein the protease is selected from the group consisting of bromelain, papain, subtilisin, and ficin.

3. The package of claim 1, wherein the enzyme is bromelain.

4. The package of claim 1, further comprising colloidal oatmeal.

5. The package of claim 1, wherein the diluent pH ranges between 7.1 and 9.0.

6. The package of claim 1, wherein the one or more enzymes is in the form of a liquid or powder.

7. The package of claim 1, further comprising a frangible or tearable seal between the opening and chamber.

8. The package of claim 5, wherein the diluent chamber comprises about 1-10 wt % sodium bicarbonate.

9. A method of treating a skin or oral condition with the package as set forth in claim 1, comprising:
   breaking the frangible or tearable barrier of the package,
   mixing the enzyme and diluent components, and
   dispensing the mixture onto a skin or oral site in need thereof.

10. The method of claim 9, wherein the skin site is selected from the group consisting of dermal irritation, itch, pain, and inflammation caused from insect bites/sting, poison ivy, poison oak, or eczema.

11. The method of claim 9, wherein the oral site is a site in need of debridement.

12. The method of claim 9, wherein the enzyme component comprises bromelain.

13. The method of claim 10, wherein the enzyme and/or diluent component further comprises colloidal oatmeal.

14. The method of claim 10, wherein the skin site in need of treatment is selected from the group consisting of contact dermatitis, idiopathic itch, diabetic itch, wound healing, jellyfish stings, psoriasis, rash, rosacea, shingles, seborrhea, chronic itch, and bruising.

15. The package of claim 1, wherein the one or more enzymes is present in an amount of 0.01 wt % to 0.22 wt %, based on total weight of the one or more enzymes and the diluent.

16. The package of claim 1, wherein the diluent comprises water, glycerol, sodium bicarbonate, a viscosity enhancing agent, and sodium benzoate.

17. The package of claim 1, wherein the sodium bicarbonate is present in an amount of 0.1 wt % to 20 wt % based on the contents of the diluent chamber.

* * * * *